US00RE37727E

(19) United States
(12) Reissued Patent
Hind

(10) Patent Number: US RE37,727 E
(45) Date of Reissued Patent: Jun. 4, 2002

(54) METHOD FOR TREATING NERVE INJURY PAIN ASSOCIATED WITH SHINGLES

(75) Inventor: Harry W. Hind, Los Altos, CA (US)

(73) Assignee: Hind Health Care, Los Altos, CA (US)

(21) Appl. No.: 09/488,195

(22) Filed: Jan. 20, 2000

Related U.S. Patent Documents

Reissue of:

(64) Patent No.: 5,709,869
Issued: Jan. 20, 1998
Appl. No.: 08/773,529
Filed: Dec. 23, 1996

U.S. Applications:

(63) Continuation of application No. 08/611,168, filed on Mar. 5, 1996, now Pat. No. 5,589,180, which is a continuation of application No. 08/388,375, filed on Feb. 14, 1995, now abandoned, which is a continuation of application No. 08/198,223, filed on Feb. 16, 1994, now Pat. No. 5,411,738, which is a continuation-in-part of application No. 07/526,771, filed on May 18, 1990, now Pat. No. 5,601,838, which is a continuation of application No. 07/325,373, filed on Mar. 17, 1989, now abandoned.

(30) Foreign Application Priority Data

| | | |
|---|---|---|
| Sep. 25, 1989 | (CA) | 612896 |
| Feb. 5, 1990 | (JP) | 2-24559 |
| Mar. 15, 1990 | (EP) | 90400699 |

(51) Int. Cl.[7] ..... A01N 25/34; A61F 13/00; A61L 15/00

(52) U.S. Cl. ..... 424/402; 424/443; 424/445; 424/447; 424/449

(58) Field of Search ..... 424/402, 443, 424/445, 447, 449

(56) References Cited

U.S. PATENT DOCUMENTS

| | | | | |
|---|---|---|---|---|
| 4,702,732 A | | 10/1987 | Powers et al. | 604/20 |
| 4,837,026 A | | 6/1989 | Raiakhyaksha | 424/449 |
| 4,880,416 A | | 11/1989 | Horiuchi | 604/307 |
| 4,895,727 A | | 1/1990 | Allen et al. | 424/642 |
| 4,937,078 A | | 6/1990 | Mezei et al. | 424/450 |
| 5,059,189 A | | 10/1991 | Cilento et al. | 604/307 |
| 5,589,180 A | | 12/1996 | Hind | 424/402 |
| 5,601,838 A | | 2/1997 | Hind | 424/443 |
| 5,709,869 A | * | 1/1998 | Hind | 424/402 |

FOREIGN PATENT DOCUMENTS

| | | |
|---|---|---|
| EP | 0276 561 | 8/1988 |
| EP | 0297 828 | 1/1989 |
| EP | 0331 392 | 9/1989 |
| GB | 1108 837 | 11/1966 |
| JP | 62-51617 | 3/1987 |
| WO | WO88/09169 | 12/1988 |

OTHER PUBLICATIONS

King (1988) Pain 33:73–78.
Russo et al. (1980) *Am. J. Hosp. Pharm.* 37:843–47.
Juhlin et al. (1980) *Acta Dermatovener* (Stockholm) 60:546–54.
Reiz et al. (1982) *Acta Anaesth. Scand.* 26:596–98.
McCafferty et al. (1988) *Br. J. Anaesth.* 60:64–69.
Lubens et al. (1974) *Am. J. Dis. Child.* 128:192–94.
Hallen et al. (1982) *Anesthesiology* 57:340–42.
Curatolo (1987) *Pharm. Res.* 4:271–77.
Dalvi et al. (1981) *J. Soc. Cosmet. Chem.* 32:87–94.
Shahi et al. (1978) *J. Pharm. Sci.* 67:789–92.
Addicks et al. (1988) *Pharm. Res.* 5:377–82.
Ostrenga et al. (1971) *J. Pharm Sci.* 60:1175–79.
Turi et al. (1979 *J. Pharm. Sci.* 68:275–79.
Barry et al. (1985) *J. Pharm. Pharmacol.* 37:84–90.
Sarpotdar et al. (1986) 75:176–81.
Hanks and White (1988) *Br. Med. J.* 297:1215.
Milligan et al. (1989) *Br. Med. J.* 298:188.
Rowotham and Fields (1989) *Pain* 297–301.
Stow et al. (1989) *Pain* 301–305.
Rowbotham (1994) *Ann. Neurol.* 36:716–23.

* cited by examiner

*Primary Examiner*—Thurman K. Page
*Assistant Examiner*—S. Howard
(74) *Attorney, Agent, or Firm*—Barbara Rae-Venter; Rae-Venter Law Group, P.C.

(57) ABSTRACT

Methods and compositions are offered for reducing nerve injury pain associated with shingles (herpes-zoster and post-herpetic neuralgia), where intradermal delivery of lidocaine is maintained for a predetermined period of time. The lidocaine appears to specifically affect the damaged nerve fibers, while leaving the undamaged and normal nerve fibers with retention of response to other stimuli. Lidocaine formulations are provided which allow for the necessary dosage of the lidocaine in the dermis during the period of treatment. The formulation may be covered with an occlusive or non-occlusive dressing, which protects the lidocaine formulation from mechanical removal and enhances the transport of the lidocaine into the dermis. Long term relief is realized after maintenance of the administration of lidocaine has been terminated.

22 Claims, No Drawings

METHOD FOR TREATING NERVE INJURY PAIN ASSOCIATED WITH SHINGLES

Matter enclosed in heavy brackets [ ] appears in the original patent but forms no part of this reissue specification; matter printed in italics indicates the additions made by reissue.

CROSS-REFERENCE TO RELATED APPLICATIONS

This is a continuation[,] of application Ser. No. 08/611,168 filed Mar. 5, 1996 and now U.S. Pat No. 5,589,180, which *is a continuation of application Ser. No. 08/388,375, filed Feb. 14, 1995, now abandoned, which is a continuation of application Ser. No. 08/198,223, filed Feb. 16, 1994, and now U.S. Pat. No. 5,411,738 which* is a continuation-in-part of application Ser. No. 07/526,771, filed May 18, 1990 now U.S. Pat. No. 5,601,838, which is a continuation of application Ser. No. 07/325,373, filed Mar. 17, 1989, now abandoned.

INTRODUCTION

Technical Field

The field of this invention is extended pain relief methods and compositions.

BACKGROUND OF THE INVENTION

The mechanism of pain generation in post-herpetic neuralgia is unknown. Post-herpetic neuralgia (PHN) begins with a cutaneous rash and the chronic state is notable for skin scarring and painfully sensitive skin (allodynia). Although the initial outbreak may be widespread, occasionally appearing to cover more than the area of skin innervated by a single dorsal root ganglion, most PHN patients are able to localize a limited area of skin as the source of their pain. PHN patients nearly always have a sensory deficit in the region obtained.

The majority of work carried out on topical agents for analgesia in recent years has been in patients with PHN. Other conditions, particularly diabetic neuropathy, have been treated in clinical trials and clinical practice with topical agents, primarily capsaicin. Topical therapies represent a very attractive alternative to oral medications for conditions like PHN. The primarily elderly patients with PHN frequently cannot be treated with tricyclic antidepressants because of pre-existing cognitive impairment, cardiac disease, or systemic illness. Diabetic autonomic disfunction may significantly enhance orthostatic hypotension from tricyclic antidepressants. Side effects like constipation, dry mouth and sedation may prove so bothersome that compliance becomes a major problem in therapy. Anticonvulsants are of uncertain efficacy in PHN, though carbamazepine and antiarrhythmics like mexiletine are effective for diabetic neuropathy. Non-narcotic analgesics are rarely effective and benzodiazepines have been proven ineffective. Opioids may be effective, but have not been adequately evaluated as long term treatment for PHN or diabetic neuropathy.

The use of local anesthetics to control the pain of herpes-zoster PHN has a history dating back to Wood's 1929 report of complete relief of ophthalmic PHN from injection of procaine into the supraorbital nerve (Wood, Am. J. Ophthalmol. (1929) 12: 759–760). Since that time, local anesthetics have been given to millions of patients by the epidural route, intravenously, as stellate ganglion blocks, as peripheral nerve and intercostal nerve blocks, and by nearly every other conceivable route to control the pain of acute zoster and PHN. Once PHN is well established, local anesthetic peripheral nerve, epidural, or synthetic blocks are unlikely to provide more than temporary relief. For such a chronic condition, it is difficult to justify highly invasive procedures, with substantial risks, just to gain hours, or at best days, of relief.

There is, therefore, substantial interest in being able to devise simple procedures which will allow for long term relief from the pain associated with herpes-zoster or PHN. Desirably, such relief should have a simple protocol, so as to minimize the continued monitoring by the patient of the treatment for pain relief. By providing for simple, easily performed protocols which do not require short term repetitive administration, elderly patients can self-administer their treatment without concerns as to adverse effects resulting from maladministration.

Relevant Literature

The following are representative of the medical literature pertaining to management of postherpetic neuralgia and herpes zoster:

Colding. A., Proc. R. Soc. Med. (1971) 66: 541–543, describes the use of local anesthetics to treat herpetic pain.

Dan, K et al., 9 Advances in Pain Research and Therapy (eds. Field et al.) (1985), pp. 831–838, describe the use of nerve block to treat herpetic pain.

Hallen, B. et al., Anesthesiology (1982) 57: 340–342, describe the use of lidocaine-prilocaine cream to reduce the pain associated with bladder catheter insertion.

Hanks and White, Br. Med. J. (1988) 297: 1215, describes local anaesthetic creams.

King, R. B., Pain (1988) 33: 73–78, describes the use of an aspirin/chloroform mixture to treat post-herpetic neuralgia and herpes zoster.

Kissin et al., Neurology (1989) 39: 1132, describes the use of topical lidocaine for relief of superficial pain in postherpetic neuralgia.

Luben, N. M. et al., Am. J. Dis. Child. (1974) 128: 92–194, describe the use of a 30% lidocaine patch for anesthesia in minor surgery.

Milligan et al., Br. Med. J. (1989) 298: 253, describe the use of a lignocaine-prilocaine cream in an anecdotal treatment of postherpetic neuralgia.

Mollgaard, B. and Hoelgaard, A., Acta. Pharm. Suec. (1983) 20:43–450 describe drug permeation formulations.

Reiz, G. M. E. E. and Reiz, S. L. A., Acta. Anaesth. Scand. (1982) 26:596–598, describe a topical anaesthetic compound.

Rowbotham and Fields, Pain (1989) 38: 297–301, describe the reduction in the pain of PHN with a topical lidocaine application.

Rowbotham, M. C., Herpes Zoster and Postherpetic Neuralgia (ed. Watson) (1993) pp. 185–203.

Russo. J. et al., Am. J. Hosp. Pharm. (1980) 37: 843–847, compare the effectiveness of different methods of lidocaine administration.

Sarpotdar, P. and Zatz, J., J. Pharm. Sciences. (1986) 75: 176–18, describe the penetration enhancement through hairless mouse skin of lidocaine by nonionic surfactants.

Secunda, L. et al., N. Engl. J. Med. (1941) 224: 501–503, describe the treatment of herpetic pain through cutaneous infiltration of local anesthetics.

Stow et al., Pain (1989) 39:301–305, describe the pharmacokinetics and efficacy of treating PHN with an EMLA cream.

Watson, C. P. et al., Neurology (1982) 32: 671–673, describe the use of amitriptyline for treatment of postherpetic neuralgia.

SUMMARY OF THE INVENTION

Methods and compositions are provided for safely reducing nerve injury pain from shingles (herpes zoster and post herpetic neuralgia) and analogous neuropathies. The methods employ lidocaine intradermal administration by transport from the skin surface for a predetermined period, whereby the lidocaine is at a dosage below that which induces anesthesia and harmful systemic side effects, during at least a substantial portion of the period of administration. The administration may be terminated, whereby extended relief is frequently obtained subsequent to the termination of the administration. Particularly, patches and dressings are employed, where the lidocaine is formulated to provide for transport of the lidocaine into the skin for a predetermined time period.

DESCRIPTION OF THE SPECIFIC EMBODIMENTS

Treatment of pain resulting from herpes-zoster infection, post-herpetic neuralgia (PHN), or other comparable neuropathies is provided. The treatment maintains an effective dosage of lidocaine intradermally for an extended period of time to maintain extended relief from pain. The relief persists during application of the source of lidocaine to the site of pain, and frequently after removal of the lidocaine source from the site of pain. The methods employ using a vehicle which allows for transport of the lidocaine across the epidermal layer into the dermal layer and maintaining an effective concentration of the lidocaine in the dermal layer for an extended period of time sufficient to relieve the pain of the patient during the treatment and frequently for an extended period thereafter. Analgesia is achieved without anaesthesia. The method may employ a dressing or protective covering and employs a formulation which provides for continual transport of lidocaine from the dressing to the dermal region at the site of pain for a sufficient period of time to provide for the extended relief during the presence of the dressing and after removal of the dressing. During the presence of the dressing, and particularly, thereafter, the affected nerves are able to respond to a wide variety of stimuli, although some deficit is noted in cold sensation. These results indicate a selective interference with "a-dela" and cold-specific "c" fiber function. Further, the results indicate that the damaged sensory fibers, particularly the heavy myelinated β-fibers, are affected in their abnormal response related to the particular neuropathy, while still being capable of responding to other stimuli in accordance with responses of normal nerve fibers. Allodynia is also diminished by the treatment. Thus, this painful skin sensitivity is also relieved.

The subject compositions and methods employ lidocaine, particularly in a form capable of transport into the dermis. Therefore, the lidocaine will be present at least in part, as the free base. The amount of lidocaine in the formulation will generally be in the range of about 1–25% (percents are by weight), more usually in the range of about 2–20%, where higher concentrations may be present in gels, generally in the range of about 2–20%, more usually 5–10%, while in plasters, the concentration will generally range from about 1–20%, more usually about 2–10%.

For the most part, the lidocaine containing formulation will be applied to the site of pain for at least about 8 to 12 hours, but not more than about 24 hours. It is found, that in some cases, after about six hours and less than about 24 hours, a mild burning sensation occurs, which indicates that the dressing should be removed. Analgesia may be maintained for at least 8 h, usually at least 12 h, desirably 24 h or more. No injury has been indicated by maintaining the dressing after the sensation, rather it is a matter of discomfort. Since the burning sensation indicates that the treatment probably has been completed, it also affords an end point for maintaining the dressing.

Various modes of application of the lidocaine formulation may be employed to ensure that a level of lidocaine is maintained for a time sufficient to substantially reduce the pain during the application of lidocaine and frequently after the application has been terminated. One formulation for intradermal delivery, which finds particular application, employs a gel. The compounds which are used will usually be substantially anhydrous, preferably anhydrous, and will frequently involve physiologically acceptable alkanols, particularly polyols, which can act as vehicles for intradermal delivery. Illustrative vehicles or solvents include alcohols, particularly ethanol and isopropanol, and polyols, particularly propylene glycol and glycerin. These alcohols and glycols may be used individually or in combination. The solvent vehicle will generally be present in from about 70–90, more commonly 70–85 weight percent.

Conventional gelling or thickening agents may be employed to provide for a formulation which can be conveniently applied to the skin. Gelling agents have been found to be effective and are illustrative of conventionally used gelling agents for skin application include Carbomer 940 (neutralized with diisopropanolamine), neutralized polyacrylic acid, etc. The gelling agent will be used in an amount sufficient to provide the appropriate viscosity, generally being in the range of about 0.1–5 weight percent. Desirably, nonionic surfactants will be included in the formulation, where the nonionic surfactants may serve as cosolvents and epidermal penetration enhancers. Conventional materials may be employed, which are physiologically acceptable, such as sorbitan esters, etc. When present, the nonionic surfactant will generally be present in an amount of from about 2–20 weight percent of the formulation.

The vehicle may also contain other physiologically acceptable excipients or other minor additives, particularly associated with organoleptic properties, such as fragrances, dyes, emulsifiers, buffers, cooling agents (e.g. menthol), antibiotics, stabilizers or the like. The excipients and minor additives will be present in conventional amounts ranging from about 0.001% to 5%, more commonly 0.001–2%, by weight, usually not exceeding a total of 10% by weight.

In some instances, one component may serve more than one function. Salicylate compounds, such as methyl salicylate or glycol salicylate, may act as co solvents and may serve as an analgesic, providing for more rapid initial relief.

The gel may be covered with an occlusive or non-occlusive dressing, which may be porous or non-porous, so as to protect the gel from mechanical removal during the period of treatment, e.g. a plastic film food wrap or other non-absorbent film. Various inert coverings may be employed, which include the various materials which may find use in plasters, described below. Alternatively, non-woven or woven coverings may be employed, particularly elastomeric coverings, which allow for heat and vapor transport. These coverings allow for cooling of the pain site, which provides for greater comfort, while protecting the gel from mechanical removal.

Instead of a gel, a plaster may be employed, where the lidocaine may be formulated with the adhesive of the plaster. In the case of plasters, the coverings may include polyvinyl chloride, polyvinylidene chlorides. (Saran®), polyethylene, synthetic rubber, woven or nonwoven polyester fabric, etc. The drug may be dissolved in the adhesive with the aid of a cosolvent, or a combination of cosolvents, such as propylene glycol, glycerin, methyl salicylate, glycol salicylate, or the like. The particular choice of adhesive is not critical, there being a wide variety of physiologically acceptable adhesives, which can maintain the lidocaine in contact with the skin for the necessary period of treatment.

The gel or plaster is applied to the site of pain and may be of any convenient size to cover the area of pain. The gel may be coated onto the skin surface and the occlusive cover applied over the gel layer, where the occlusive cover will have a physiologically acceptable adhesive along its edges. The plaster may come in large sheets, e.g. 10×14 cm patches, which may be cut to the appropriate size or in a variety of sizes. Once the dressing is applied it will usually be left for an extended period of time, where onset of relief is fairly rapid, usually within 0.5 to 4 h. Removal of the dressing will usually occur within about 6 to 24 h, during which period significant relief is achieved as compared to the absence of the dressing. In some patients, relief is maintained after removal of the dressing for up to two weeks or more. Where pain returns after the treatment, the dressing may be reapplied and provides a reduction in pain, without significant loss of response due to the prior treatment, which loss of response is frequently observed with analgesics.

The following examples are offered by way of illustration and not by way of limitation.

EXPERIMENTAL

First Study

Methods

Patients

Claims for the effectiveness of the invention are supported by the results of a study undertaken by Rowbotham, M. C. and Fields, H. L., Department of Neurology, School of Medicine, University of California, San Francisco. This study entitled "Topical Lidocaine Reduces Pain in PostHerpetic Neuralgia", Pain (1989) 38:297–301, presents data from experience with 11 patients who had well-established post-herpetic neuralgia (pain present for more than 3 months after healing of the rash of herpes zoster); well-demarcated areas of skin with marked allodynia (pain resulting from a nonnoxious stimulus to normal skin) from light stroking with a cotton wisp: and no medical contraindications to the use of local anesthetics.

Six women and five men participated in the study. The average was 70 years. Six patients had post-herpetic neuralgia that included the ophthalmic division of the trigeminal nerve, and five had postherpetic neuralgia located in thoracic dermatomes.

The duration of pain ranged from 3 months to 12 years.

All subjects except two were in good general health. One patient had multiple cardiovascular problems, and another had widespread multiple myeloma.

In all cases, post-herpetic neuralgia was the only significant pain problem during the period of the study.

Formulation of Analgesic Containing Compound

The local anesthetic preparation used in the study consisted of 10% lidocaine in a gel vehicle. The vehicle consisted of 12% polysorbate-20, 0.9% carbomer 940, 0.8% diisopropanolamine, and 76.3% propylene glycol. Lidocaine gel was applied to the skin, and the area was covered with plastic food wrap. (Saran® Wrap) and the edges taped with 3M Micropore Adhesive Tape; taking care not to apply tape to hypersensitive skin.

Application of Compound

For thoracic post-herpetic neuralgia, the dosage of lidocaine applied as gel ranged from 240 to 500 mg.

Subjects with post-herpetic neuralgia involving the trigeminal nerve were not treated in the same way. Instead, the gel provided was spread by the subject over areas of maximum pain and sensitivity on the forehead, temple, and scalp. The medication was not covered. Instead the medication was applied repeatedly to maintain contact. The dosage of lidocaine applied in this way ranged from 140 to 300 mg.

Pain Measurement

Pain was measured on the 100 mm pain VAS scale and a 100 mm pain relief VAS scale. The VAS (Visual Analog Scale) pain scale is defined in Littman, G. S., et al., Clin. Pharmacol. Ther. (1985) 38: 16–23. Pain levels were assessed every hour for 4 hours after lidocaine application. Blood pressures and pulse rates were recorded, and possible side effects were monitored. At 1 and 3 hours after lidocaine application, blood was drawn for determination of serum lidocaine levels.

Results

For the entire group of 11 subjects, pain VAS ratings declined steadily over the 4 hours of observation from a baseline mean of 35.5 mm+/−25.4 mm to a low of 14.2 mm+/−7.8 mm at 4 hours after application ($P<0.01$). Pain relief VAS ratings increased steadily during the observation period from 39.3 mm+/−39.9 nmm at 1 hour after application to 59.6 mm+/−25.5 mm at 4 hours after application ($P=0.01$). Calculating the change in pain VAS scores from baseline for the observation period showed the largest decrease in pain score occurred at 3 hours after gel application. The decrease was 21.2 mm+/−19.4 mm ($P=0.05$).

There were significant differences in the manner in which patients with thoracic post-herpetic neuralgia and those with trigeminal post-herpetic neuralgia responded to the topical lidocaine. The five subjects with thoracic post-herpetic neuralgia had highly significant changes in pain ratings, especially during the last 2 hours of observation, from a baseline mean of 44.2 mm+/−21.6 mm to a low of 12.8 mm+/−8.7 mm ($P=0.001$). The results achieved with occlusive dressings and with the plaster formulation described below in the second and third studies were equally good.

Subjects with trigeminal post-herpetic neuralgia also demonstrated a decline in pain VAS scores, but the observed changes were not statistically significant.

Analysis of pain relief also showed a difference in response between the two groups, but in both groups the mean peak pain relief ratings were greater than 50 mm. The greater pain relief experienced by the patients with thoracic post-herpetic neuralgia may be attributed to the enhancing effect of the occlusive covering.

Subjects reported no adverse effects of topical lidocaine during the period of the study. Changes in blood pressure and pulse were not significant. At both 1 and 3 hours after application, serologic tests revealed measurable blood levels of lidocaine in all subjects, but the concentration in all cases was below 1 microgram per milliliter.

Second Study

Methods

Patients

Subjects were eligible if they had pain present more than 1 month after healing of the zoster skin rash, had a well defined area of painfully sensitive skin, were in stable health, had no medical contraindications to topical local anesthetic application, and had not previously undergone neurolytic or neurosurgical therapy for PHN.

Any use of topical medications for PHN, including capsaicin and steroids, was discontinued at least one week prior to the first study session. During the study, subjects were not allowed to use any topical medications on the area affected by PHN. Subjects were allowed to continue use of oral medications for control of PHN pain, including "as needed" analgesics, but were not allowed to start new oral medications during the study.

All subjects gave informed consent prior to participation, and the study was approved by the Committee on Human Research at the University of California, San Francisco (UCSF).

Study Sessions

All sessions were carried out at the UCSF Pain Clinical Research Center. Subjects with PHN affecting the head or neck had gel applied without occlusion (cranial group) and sessions lasted 8 hours. Subjects with PHN of the limbs or torso had gel applied under Tegaderm™ occlusion (torso-limb group) and sessions lasted 24 hours. One session type (local) consisted of 5% lidocaine gel applied to the painful skin area and vehicle placebo application to the matching contralateral skin area. One session type (remote) consisted of vehicle placebo application to the painful skin area and 5% lidocaine gel application to the matching contralateral skin area. One session type (placebo) consisted of vehicle placebo application to both the painful skin area and the matching contralateral skin area. Subjects were randomly assigned to one of the six possible treatment orders (local-remote-placebo, placebo-local-remote, etc).

All sessions were carried out in an identical double-blind manner. Sessions were at least 72 hours apart and were usually scheduled one week apart. If subjects experienced prolonged relief from one of the sessions, the next session was delayed until pain returned to at least 75% of their average pain level prior to entering the study. If skin irritation was noted at the end of a session, the subject was re-examined the following day and further test sessions were postponed until skin irritation resolved fully. Subjects were dropped from the study if all 3 sessions could not be completed within a 42 day time period.

Subjects remained in the vicinity of the UCSF Pain Clinical Research Center for the first 8 hours after gel application. After 8 hour ratings and skin examination, the subjects in the cranial group had gel removed and went home. After 8 hour ratings and skin examination for the torso-limb group, subjects went home and returned the following morning for final (24 hour) ratings followed by gel removal and skin examination, including sensory examination.

Drug Application

Lidocaine 5% gel (lidocaine (5.15%), propylene glycol (81.25%), Carbomer 940 (0.8%) and diisopropylamine (0.8%)) was employed. Vehicle placebo gel was identical except for the absence of lidocaine.

The investigators wore gloves for gel application and removal. Prior to gel application in the occlusion group, the painful area to be treated was marked (and then photographed) based on the subject's report of the borders of the maximally painful area corroborated by testing for allodynia by lightly stroking the skin with a cotton swab. Tegaderm™, is a clear, thin, stretchy, and self-adherent occlusive dressing. Sheets measuring 20×30 cm were used. The sheets were cut so that after the gel was applied to the painful area, the Tegaderm™ dressing would seal the area with an approximate 2 cm border around the gel application area. The procedure would then be repeated on the contralateral normal skin. Up to 800 $cm^2$ of skin was covered with gel on each side of the body. Prior to gel application to the face or neck, the borders of the painful area were delineated based on the subject's report and corroborated by testing for allodynia from lightly stroking the skin with a cotton swab. At most, an area of 200 $cm^2$ on each side was covered with gel.

Measures

Pain intensity ratings using a 100-mm visual analog scale (VAS) were completed twice prior to gel application. For the cranial group, VAS ratings were made at 30 minutes, 1 hour, 2 hours, 3 hours, 4 hours, and 8 hours after application. For the torso-limb group, VAS ratings were made at 30 minutes, 1 hour, 2 hours, 4 hours, 8 hours, and 24 hours after application. A 6 item category scale of pain relief (worse, no relief, slight, moderate, a lot, and complete relief) was completed at the same time following application as was the VAS pain scale. A 27 item checklist of side effects (maximum score 81), primarily designed to detect symptoms of systemic local anesthetic administration or other systemic medication effects, was completed at the same time as the completion of the pain VAS.

A clinical sensory examination of the area of pain, primarily to document the severity of allodynia, was carried out prior to gel application and repeated after gel removal. Allodynia, defined as a painful sensation elicited by gentle moving mechanical stimulation that is innocuous in normal skin areas, was rated as absent (0), mild (+1), moderate (+2), or severe (+3). Examination of the skin for signs of skin irritation was carried out prior to gel application, at the 8 hour ratings (the occlusive dressing is clear), and after gel removal. Blood pressure and pulse were measured twice prior to gel application and repeated at 1, 4, and 8 hours after gel application in the cranial group. Blood pressure and pulse were measured twice prior to gel application and repeated at 1, 4, 8, and 24 hours after gel application in the torso-limb group.

Blood Lidocaine Levels

Blood lidocaine levels were measured prior to gel application and at 1, 4, and 8 hours after gel application in the cranial group. An additional blood lidocaine level was obtained at 24 hours in the torso-limb group. For the majority of sessions, lidocaine was assayed using an antigen antibody assay sensitive to levels as low as 0.1 mcg/ml (TDx system, Abbott Laboratories Inc.). For 15% of the subject sessions, lidocaine levels were measured in the laboratory of Dr. Peyton Jacob III at San Francisco General Hospital using a capillary gas chromatography assay that is linear from lidocaine concentrations of 0.01 mcg/ml to 1.0 mcg/ml. This assay uses carbocaine as an internal standard with an extraction method adapted from the method described in Jacob et al., Biol. Mass Spectrom. (1991) 20: 247–252.

Data Analysis

Statistical consultation was obtained from John S. Quiring, Ph.D. of QST Consultation, Ltd., Allendale, Mich. Because of the slightly differing protocols for occlusion and non-occlusion subjects, results for the two groups were analyzed separately. The primary variables of interest were the pain VAS scores and the category pain relief scores. The primary comparison was between the session with lidocaine gel on the painful area and the session with placebo vehicle on both sides. Symptom checklist scores, blood pressure and pulse rates were handled in the same way as the pain VAS and pain relief scores.

The method of analysis of variance (ANOVA) was used to analyze all study variables at each sampling time. This was accomplished using the Statistical Analysis System (SAS) version 6.04, under the procedure General Linear Models. The analysis of the study variables for all 3 sessions was based on an ANOVA which corresponded to the three-way crossover design. The statistical model included the effects of subject (nested within sequence), treatment, sequence and session. A hypothesis test was conducted to determine if there was any evidence of a carryover (sequence) or residual effect of the treatment administered in one session on the results observed in the next session.

The p-value for testing the equality of the local and placebo treatments was derived from the F test using the pooled ANOVA Type III mean square error in the hypothesis test statement. The least squares means, which were obtained by application of ANOVA, were considered the best unbiased estimate of the subject's mean values considering the subject, sequence, and sessions effects present in the trial. The difference between placebo and local sessions were considered to be statistically significant when the p-value was less than 0.05. The change from pre-treatment was computed as the pre-treatment score minus the post-treatment score. If a subject had more than one pre-treatment score, they were averaged.

Results

Subjects

Fifty subjects were recruited for participation in the study. Thirty-nine subjects completed all 3 sessions without protocol violation or ineligibility and are included in the data analysis as valuable subjects. Three subjects were recruited but did not give written consent and so did not begin any study sessions. One subject was found ineligible due to incorrect diagnosis. Two subjects repeatedly used medicated topical agents and were dropped from the study. Two subjects experienced skin redness and tenderness after the first session and declined to return for further sessions; both had received placebo vehicle application and had adhesive abrasions from Tegaderm removal. One subject reported a general flare in pain in the days following the first session without localized skin reaction and declined to return for further sessions; she had received lidocaine gel on the painful area Two subjects could not complete the study within the 6 week limit; one because of scheduling problems and the other because of prolonged relief from the second session.

Seven men and 9 women in the cranial group completed the study. Their average age was 75 years (range 62–85), and their average duration of PHN was 36 months (range 6–137 months). Two subjects had PHN in the C2/C3 dermatomes, the remainder in the first trigeminal division. The average area of affected skin treated with gel was 103 $cm^2$. From 2.5 to 12.0 grams of gel (125–600 mg lidocaine base) was used to fully cover the area of pain.

Eleven men and 12 women in the torso-limb group completed the study. Their average age was 70 years (range 55–83), and their average duration of PHN was 23 months (range 4–75 months). Three patients had PHN primarily affecting the upper arm, one subject had PHN primarily affecting the posterior thigh, and the remaining nineteen had PHN affecting the thoraco-abdominal region. The average area of affected skin treated with gel was 297 $cm^2$, with the maximum area of skin covered by gel being 800 $cm^2$. From 6.5 to 12.5 grams of gel (325–625 mg lidocaine base) was used to fully cover the area of pain.

Pain Intensity VAS (Visual Analog Scale) Ratings

In the cranial group, pre-application VAS scores were 38.8 mm for the local session, 45.0 for the placebo session, and 42.7 mm for the remote session; these differences were not significant. Pain intensity VAS scores changed little during the first three hours. At the 4 hour rating, VAS scores fell by more than 10 mm in both the local and placebo sessions, but only in the local session was the reduced VAS score maintained to the 8 hour rating. Comparing both the local and placebo sessions, and both the remote and placebo sessions, none of the post-application VAS scores differed significantly.

In the torso-limb group, pre-application VAS scores were 51.4 mm for the local session, 49.3 for the placebo sessions and 48.4 mm for the remote session; these differences were not significant. Pain intensity ratings declined steadily during the first 2 hours after gel application during all three session types, but declined most during the local session. Pain ratings then gradually returned toward the pre-application baseline during both the placebo and remote sessions. During the local session, pain VAS scores continued to decline during the rest of the 24 hours observation to levels of 13.2, 13.8, and 14.6 mm below baseline at the 4 hour, 8 hour, and 24 hour ratings. Comparing the local and placebo sessions, there was a statistically significant reduction in pain VAS ratings at 8 hours (p=0.048) and 24 hours (p=0.024) during the local session. There were no significant differences between the remote and placebo sessions.

Pain Relief Category Scores

In the cranial group, mean relief ratings varied between "no relief" and "slight relief" in both the placebo and remote sessions during the eight hours of observation. Mean relief ratings during the local session were consistently higher than in the placebo and remote sessions, varying between "slight relief" and "moderate relief" at the 2 hour, 3 hour, 4 hour, and 8 hour ratings. Comparing the local and placebo sessions, there was statistically significant pain relief during the local session at 30 minutes (p=0.046), 2 hours (p=0.010), 4 hours (p=0.033), and 8 hours (p=0.003).

In the torso-limb group, mean relief ratings clustered around "slight relief" during the first four hours after application during all three session types. Thereafter, relief ratings were greatest during the local session, reaching the mid-way point between "slight relief" and "moderate relief" at 24 hours. Comparing the local and placebo sessions, pain relief during the local session approached statistical significance at 8 hours (p=0.053) and was significant at 24 hours (p=0.012).

Changes in Allodynia Following Gel Application

No subject had normal sensation in the area of pain prior to gel application, as at least mild allodynia was a requirement of study participation. In addition to the presence of allodynia, all subjects had subjective asymmetries in one or more modalities of detection threshold to light touch with a cotton wisp, perception of gentle pinprick, and perception of a chilled metal disc applied within the area of maximum pain. Mean allodynia ratings prior to gel application ranged between 2.1 and 2.2 for all 3 session types, indicating moderate to severe allodynia. Allodynia declined by a mean of 0.47 grades after local gel application, by 0.14 grades after placebo application, and by 0.31 grades with remote lidocaine gel application. Local gel application reduced allodynia significantly more than placebo gel application (Wilcoxon signed ranks test, p=0.021).

Skin Reactions

Mild and transient reddening of the skin was the most common skin reaction observable after gel application. No difference was observed in frequency between active gel and placebo vehicle; subjects who displayed mild skin reddening frequently developed it with both active and placebo application, indicating a reaction to a component in the vehicle. Of the total 47 subjects (134 total sessions) who had gel applied on at least one session, 29 subjects had no skin reddening during or after any session. Reddening lasting more than 24 hours was reported or observed in 3 subjects, with none developing skin breakdown. In the torso-limb group where occlusion was provided using Tegaderm™, abrasions from the removal of the covering was a more significant problem; adhesive abrasions were reported by 9 subjects and in 2 were sufficient to cause them to drop out of the study.

Symptom Checklist Scores

Prior to drug application, most items checked on the 27 item symptom checklist (SCL) reflected either tricyclic antidepressant side effects or primary symptoms of PHN, such as "itching" and "burning skin". Pre-application SCL scores were low in both the cranial and torso-limb groups for all session types (range of least square means 2.9 to 4.6 out of a possible maximum of 81). After drug application, mean SCL score changes were small (range −0.3 to +2.6), indicating an absence of systemic local anesthetic type side effects from lidocaine gel application on either the area of pain or the contralateral matching skin area. The number of subjects who reported "itching" and "burning skin" declined during the local session in both the cranial and torso-limb groups. In the torso-limb group at 24 hours after application, the SCL was significantly lower during the local session than during the placebo session.

Blood Pressure and Pulse Measurements

There were minor changes in systolic and diastolic blood pressure, and in pulse rate, during the study sessions. Least square mean changes in systolic blood pressure varied between −11 and +2 mm Hg. Least square mean changes in diastolic blood pressure varied between −5 and +5 mm Hg. Least square mean changes in pulse varied between −5 and +10 beats per minute. The changes observed did not appear to be related to session type or drug application. In the torso limb group, both systolic and diastolic blood pressure declined to a greater degree during the local session than in the placebo session, reaching statistical significance for diastolic blood pressure at 24 hours.

Lidocaine Blood Levels

Blood lidocaine levels were all below 0.6 micrograms/ml. Of the 42 subjects who had any blood lidocaine levels during local or remote sessions determined with the TDx assay, only 8 had any blood concentrations exceeding 0.1 mcg/ml, with the highest measured level being 0.29 mcg/ml. The TDx antigen-antibody assay cannot quantitate reliably enough below 0.1 mcg/ml to calculate any pharmacokinetic parameters.

Of the 13 subjects who had any blood lidocaine levels determined by the more sensitive capillary gas chromatography (quantitation limit 0.01 mcg/ml), only 3 had any levels exceeding 0.1 mcg/ml with the highest recorded level being 0.59 mcg/ml. By gas chromatography, measurable blood lidocaine was present at 1 hour after lidocaine gel application in only 2 of the 13 subjects. Seven of the 13 subjects did not have measurable blood lidocaine until the 8 hour blood sample. As only 3 subjects in the cranial group had lidocaine levels determined by the gas chromatography method, no absorption comparison can be made between lidocaine gel application on the highly vascular facial skin without occlusion and the thicker, less vascular skin on the torso with an occlusive dressing. There were 5 subjects who had both the local and remote sessions analyzed by the gas chromatography technique. Blood lidocaine levels during the two sessions in these 5 subjects were highly correlated (R squared=0.940, p=0.006), indicating that if systematic differences in lidocaine absorption across intact vs. postherpetic skin exist, they must be small.

Discussion

Lidocaine gel 5% produced significant reductions in pain intensity and significant pain relief when applied under occlusion to the torso or limbs for a period of 24 hours. When applied to the face, head, or neck region without occlusion for a period of 8 hours, significant pain relief was reported. Although complete anesthesia of the skin was not apparent after prolonged application, there was a significant reduction in allodynia with local gel application on the painful skin. No systemic side effects were reported. Local side effects consisted of mild and transient skin reddening, most likely due to the anhydrous nature of the vehicle and its components, and adhesive abrasions from the occlusive dressing used. Although there is measurable uptake of lidocaine into the venous circulation in some patients, the levels are low. Even after 24 hours of contact under occlusion, venous lidocaine levels never entered the reported range of 0.6–2.0 mcg/ml minimum concentrations of lidocaine for anti-arrhythmic effects. Systemic absorption was nearly identical in normal and post-herpetic skin.

Skin thickness and vascularity undoubtedly play a significant role in determining the time of onset and duration of analgesia observed in the present study. Arendt-Nielsen and Bjerring have elegantly demonstrated such relationships for EMLA™ (Eutectic Mixture of Local Anesthetics) under occlusion using high energy heat stimulation of the skin of the hand dorsum, cheek, forehead, antecubital fossa, and low back with an argon laser. (EMLA provides for anaesthesia as the mode of pain relief.) Arrendt-Nielsen and Bjerring, Anesth. Analg., (1988) 67: 115,123. Areas with thick stratum corneum, such as the hand and antecubital fossa, had a slower onset of analgesia than the back, which has a thinner epidermis but similar blood flow. Areas of high vascularity, such as the forehead, had a rapid onset of analgesia but a reduced efficacy and short duration. This finding can be explained by the location of the main portion of the cutaneous free nerve endings (which includes unmyelinated nociceptors) at the dermal-epidermal junction close to the papillary capillaries. If the vascular uptake of local anesthetic is high, the concentration in the microenvironment around the nerve endings will remain low and produce inadequate analgesia. Vascularity is also an important determinant of the duration of analgesic effect. In areas of relatively low blood flow, analgesia may continue for a time after the drug is removed from the skin surface because the skin acts as a drug reservoir. In areas of high vascularity, the rate of vascular uptake may be equal to influx of drug through the skin and no reservoir is formed. In the present study, consistent with the more rapid drug penetration through the skin of the forehead, subjects with cranial PHN reported significant pain relief from lidocaine gel application on painful skin beginning at 30 minutes, 2,4, and 8 hour ratings of the 8 hour session. When applied to the torso or limbs, pain relief was significant and long lasting, but of apparently slower onset. The greatest difference from placebo in pain intensity and relief ratings occurred at 24 hours.

Pain intensity ratings declined during the first two hours in all 3 session types when gel was applied under occlusion. This is most likely due to the relative immobility of the patients during the observation period and the protective effect of gel covered by Tegaderm™ occlusion. This prevents the type of gentle mechanical deformation of hair follicles and skin that produces allodynia on examination and is reported by patients as painful sensitivity to touch and wearing clothing. Later during the sessions, pain ratings returned toward baseline when placebo vehicle had been applied on painful skin but pain continued to lessen in those sessions where active lidocaine gel had been applied on the painful skin. This divergence between lidocaine gel and vehicle took place at about the time that measurable blood lidocaine levels appeared. Thus, lidocaine penetration and intradermal reservoir formation probably takes place over several hours in the low vascularity, thicker stratum corneum skin areas where gel was applied under occlusion. Once established, it then persists for the remainder of the 24 hours of application and is correlated with the prolonged pain relief observed.

The primary comparison was between the local session, in which lidocaine gel was applied to the painful area and vehicle to the contralateral matching skin area, and the placebo session, in which vehicle was applied bilaterally.

Comparing the remote session, in which lidocaine gel was applied to the contralateral normal skin, to the placebo session showed no significant differences in pain intensity or pain relief. This demonstrates that a local action of lidocaine on the painful skin is necessary for its pain relieving action.

Primary afferents, including nociceptors, in damaged peripheral nerves have lowered thresholds and develop spontaneous activity. These changes may be due in part to the increased expression of voltage sensitive sodium channels which are the target of local anesthetics. In fact, the spontaneous activity that develops in damaged primary afferents is blocked by local anesthetics at concentrations lower than required to block impulse propagation in undamaged axons. It appears likely that with topical application of lidocaine, the tissue concentrations of the drug in the region of cutaneous nerve endings would be high enough to block abnormal spontaneous discharge without the production of a dense cutaneous anesthesia.

The 50 subjects initially recruited for this study have been followed for up to 30 months. Forty-two of the 50 elected to try topical lidocaine in open-label use. Six subjects reported minor redness and skin irritation. Thirty-one subjects used topical lidocaine for more than 2 months, and 23 of these 31 subjects reported moderate or better pain relief by follow-up examination and/or questionnaire.

Third Study

In a further refinement for thoracic postherpetic neuralgia, an adhesive plaster sheet (10×14 cm), with a non-woven polyester fabric backing and 14 grams of adhesive containing 5% lidocaine was applied to affected areas of the torso of patients. The plaster formulation was found to be as effective as the occlusive dressing formulation in relieving pain associated with thoracic post-herpetic neuralgia.

Methods

Patients

Subjects were eligible if they had PHN, defined as pain present more than 1 month after healing of the skin rash, had a well defined area of painfully sensitive skin on the torso or limbs, were in stable health, had no medical contraindications to topical local anesthetic application, and had not undergone neurolytic or neurosurgical therapy for PHN.

Any use of topical medications for PHN, including capsaicin and steroids; was discontinued at least one week prior to the first study session. During the study, subjects were not allowed to use any topically applied medications, salves; etc., on the area affected by PHN. Subjects were allowed to continue use of oral medications for control of PHN pain, including "as needed" analgesics, but were not allowed to start new oral medications during the study.

All subjects gave informed consent prior to participation, and the study was approved by the Committee on Human Research at the University of California, San Francisco (UCSF).

Study Sessions

Four clinical sessions were conducted: one observation session, one placebo session, and two "active" sessions. All sessions were carried out at the UCSF Pain Clinical Research Center. All sessions requiring patch application were carried out in an identical manner. Data collection for the no-treatment, observation only session followed the same format as for patch application sessions except no blood was drawn for lidocaine level. Sessions were at least 72 hours apart and were typically scheduled 1 week apart. If a subject experienced prolonged relief from one of the sessions, the next session was delayed until pain returned to at least 75% of their average pain level prior to entering the study. If skin irritation was noted at the end of a session, the subject was re-examined the following day and further test sessions were postponed until skin irritation resolved fully. Subjects were dropped from the study if all 4 sessions could not be completed within a 42 day time period.

Subjects remained in the vicinity of the Pain Clinical Research Center for the first 6 hours of patch application or no-treatment observation. After 6 hour examination, including blood drawing and brief removal of the patches for skin inspection and sensory examination, the patches were reapplied and the subjects were sent home. At home, the subjects made additional ratings of pain, pain relief, and side effects at 9 hours and 12 hours after initial application before finally removing the patches.

Study Drug and Placebo

Lidocaine patches (Lidoderm Patch) contain an adhesive of 5% lidocaine base (700 mg/patch), water, glycerin, D-sorbitol, sodium polyacrylate, sodium carboxymethylcellulose, propylene glycol and other ingredients on a non-woven polyester backing. Vehicle placebo patches are identical except for the absence of lidocaine. The size of a single patch is 10×14 cm.

Patch Application

Prior to patch application, the painful area to be treated was marked and then photographed based on the subject's report of (1) the borders of the area of sensory abnormality, and (2) the area of greatest pain. Up to 3 patches were applied to cover the area of greatest pain as fully as possible within the limit of 420 $cm^2$ of patch area.

Pain Ratings

Pain intensity was assessed using a horizontal 100 mm visual analog scale (VAS). The subject indicated the severity of his or her pain with a mark along the line between "no pain" (0 mm) and "worst pain imaginable" (100 mm). Prior to patch application, VAS scores were obtained 3 times over a 45 minute period; one before quantitative sensory testing ("QST") and two after QST. For a minority of subjects, only 2 VAS scores were obtained; one before and one after QST. After patch application, VAS scores were obtained at 30 minutes, 1 hour, 2 hours, 4 hours, 6 hours, 9 hours, and 12 hours.

Pain relief was assessed using a category scale consisting of 6 sentences indicating that: the pain is increasing (score 0), "no" pain relief (1), "slight" pain relief (2), "moderate" pain relief (3), "a lot" of pain relief (4), and "complete" relief of pain (5). As the scale is designed to assess changes only, there is no baseline pre-application rating. Because no patches were applied during the no-treatment, observation only session, the scale was slightly modified to indicate worsening or improvement relative to the beginning of the observation session. After patch application, category relief scores were obtained at 30 minutes, 1 hour, 2 hours, 4 hours, 6 hours, 9 hours, and 12 hours.

Sensory Testing

Prior to patch application, a non-quantitative sensory examination of the area of greatest pain was carried out. The unaffected matching contrilateral skin area was used for comparison. Allodynia to light stroking and pressure on the skin with a cotton swab was graded as absent (0), mildly painful (+1), moderately painful (2+), or severely painful (+3). This type of stimulation primarily activates cutaneous mechanoreceptors, both static and dynamic. Perception of pinprick using a common safety pin was graded as severely reduced/absent (−2), reduced (−1), normal (0), mildly hyperalgesic (+1), and moderately/severely hyperalgesic (+2). With the type of pin stimulation used, the perception is primarily mediated by a-delta sensory fibers. Perception of cold using a 3 cm diameter metal disc chilled to 10° C. was graded with the same scale. At this temperature, a mixture of c-cold thermoceptors, c-nociceptors, and a-delta sensory fibers are activated. The non-quantitative sensory examination was repeated during the time the patches were temporarily removed from the skin after the 6 hour ratings and blood drawing.

After the non-quantitative sensory examination was carried out, quantitative thermal sensory testing (QST) was carried out using the Somedic Thermotest (Somedic AB, Stockholm). The 12 $cm^2$ surface area thermode employing a Peltier principle is designed to heat up at a linear rate to a machine-determined cut-off of 51° C. and cool down to a machine-determined cut-off of 4° C. The cut-off temperatures are to prevent thermal skin injury in subjects unable to detect thermal stimulation. Three locations were identified and marked within the area of greatest pain for QST. The matching (non-painful) contralateral skin locations were tested as reference points. The subject holds a button that, when pressed, returns the thermode temperature to the holding temperature of 30° C. Beginning in the non-painful contralateral skin area, the thresholds were determined in the three locations to probe warming (warm threshold, WT), followed by heat pain perception (heat pain, HP), probe cooling (cold threshold, CT) and cold pain perception (cold pain, CP). The marked locations in the area of greatest pain were then tested in the identical manner. The threshold to warming (WT) represents activation of c-warm thermoceptors. The threshold to heat pain (HP) represents activation of c-nociceptors. The threshold to cooling (CT) is thought to represent selective activation of a-delta and c-cold thermoceptors. The threshold to cold pain represents activation of c-nociceptors. After 6 hours of patch application, QST examination was repeated in the identical skin locations.

Symptom Checklist (SCL) and Skin Inspection

In addition to physical examination of the skin when the patches were briefly removed after 6 hours, side effects were rated using a written list of 27 items (maximum score 81). Some of the symptoms were included to screen for high dose intravenous local anesthetic effects, though most overlap with common effects of tricyclic antidepressants and systemic analgesics. A reduction in SCL can reflect an improved sense of well-being.

Blood Lidocaine Levels

Blood samples were drawn into heparinized tubes prior to patch application and at 1 hour, 4 hours, and 6 hours after patch application. The blood was centrifuged and the plasma extracted and kept at 0° C. until transfer to a −20° C. freezer for longer term storage before assay. Venous blood lidocaine was assayed using one of two techniques. The TDx system (Abbott Laboratories) is an antigen-antibody assay sensitive to levels as low as 10 nanograms/ml, but only able to reliably quantitate above 100 nanograms/ml. The usual minimum anti-arrhythmic concentration of lidocaine in the venous circulation is 1.0–1.5 micrograms/ml, or 1000–1500 nanograms/ml. A more sensitive assay was performed in the Clinical Pharmacology Laboratory at San Francisco General Hospital using capillary gas chromatography with nitrogen-phosphorus detection that reliably quantitates to levels as low as 10 nanograms/ml. This assay uses carbocaine as an internal standard with an extraction modified from the method of Jacob and co-workers. Jacob et al., Biological Mass Spectrometry (1991) 20: 247–252.

Data Analysis

The statistical analysis strategy was developed prior to study initiation in consultation with John S. Quiring, Ph.D., who also carried out all data analysis except for non-parametric analysis of non-quantitative sensory testing results. The method of analysis of variance was used whenever possible. This was accomplished using the Statistical Analysis System (SAS) v.6.04, under the procedure General Linear Models. The analysis was based on an analysis of variance ("ANOVA") which corresponded to the four-way crossover design with treatments at three levels: active, placebo, and observational. For analysis purposes the first and second active sessions were coded together as active. The statistical model included the effects of patient (nested within sequence), treatment, sequence and session. A hypothesis test was conducted to determine if there was any evidence of a carryover (sequence) or residual effect of the treatment administered in one session on the results observed in the next session. The least squares means, obtained by application of ANOVA, were used as the best unbiased estimate of the patients' mean values considering the patient, sequence, and session effects present in the study.

All tests of hypotheses which evaluated the equality of treatments were based on the type III mean square error terms. An overall F-test was conducted to determine if there were differences among the three treatments. Additionally, pairwise contrast tests between treatments were performed to evaluate the statistical significance between pairs of treatments. The difference between two treatments (F-test) was considered statistically significant if both the overall and pairwise p-values were less than or equal to 0.05. For pain intensity VAS scores, QST data, and SCL scores, the pairwise comparisons were made at individual time points in addition to the overall F-test. For the limited number of rating choices present in the category relief scores, the scores were averaged over all time points after patch application for pairwise comparison in addition to the overall F-test.

Two complete analyses were performed. One was based on the crossover design in all subjects who completed the study without protocol violation. The second one, an intent to treat analysis, was based on all subjects entering the study using only the data from the first session. In the intent to treat analysis, a one-way analysis of variance was used to evaluate pairwise differences between treatments. Although the intent to treat analysis is free of any possible carryover or residual effects, statistical significance is generally weaker because only the data from the first of the four sessions is used in the analysis.

ANOVA for the QST data was carried out using the median value for each threshold on each side of the body. The median value of the three locations was selected to represent the central tendency for that area instead of the mean because it is less sensitive to the machine safety cut-off values for outliers. For non-quantitative sensory testing data, the Wilcoxon signed ranks test for paired data was applied to the change in each value from baseline.

Results

Subjects

Forty subjects were recruited and entered the study. There were 22 males and 18 females. The age range was 52 to 90 years; the men averaged 73 years and the women 78 years. There was one African-American, one Hispanic, and one Asian subject; the remainder were Caucasian. The duration of PHN ranged from 4 to 276 months, averaging 76 months. The range of size of the affected area was 36 to 851 $cm^2$. averaging 230 $cm^2$.

Thirty-five subjects completed the study. Of the five subjects who did not complete the study, one was dropped after the first (observation) session because of lack of allodynia, two dropped out of the study after the first (observation) session because of fatigue and pain; one was dropped from the study after completing two sessions (active and observation) because severe depression interfered with obtaining reliable ratings, and one withdrew consent before beginning any session.

Pain Ratings

Pre-treatment, the least square mean pain intensity VAS scores were 49.3 mm for active sessions, 48.4 mm for placebo vehicle patch sessions, and 47.2 mm for observation only sessions. These pre-treatment differences were not significant. During the active sessions, the greatest reduction in VAS pain intensity was 12.3 mm at the 4 hour time point, with the average reduction in VAS across all time points being 10.2 min. Compared to observation only, active patch application significantly reduced pain at all time points 30 minutes to 12 hours (individual time points p=0.0001 to p=0.021). Compared to placebo vehicle patch, active patch application significantly reduced pain at time points 4 hours, 6 hours, 9 hours, and 12 hours (individual time points p<0.001 to p=0.038). Placebo vehicle patch significantly reduced pain compared to observation only at times 2 hours and 6 hours (individual time points p=0.016 and p=0.041).

Category pain relief scores were highest for active patch application at all time points 30 minutes through 12 hours. The least square mean of the average pain relief rating was 2.17, between "slight" and "moderate" relief, with the highest relief ratings of 2.44 at 4 hours after application. Active patch application produced significantly higher average pain relief scores than observation only (p<0.0001) and placebo vehicle patch (p=0.033). Placebo vehicle patch and observation only average pain relief scores were also significantly different (p=0.001).

Sensory Testing

Baseline non-quantitative sensory testing was abnormal in all subjects in the area of pain. All subjects had allodynia in the area of pain. At the beginning of the observation session, only 2 subjects reported normal perception of pinprick and 4 subjects reported normal sensation to the chilled metal disc. Using a scale ranging from −2 (markedly decreased or absent perception) to +2 (markedly increased, i.e., hyperesthetic or hyperalgesic), the mean sensitivity to pin-prick at the beginning of each session ranged from −0.70 to −0.91. The mean sensitivity to a cold stimulus ranged from −0.32 to −0.66. The mean allodynia rating ranged from 1.83 to 2.07. The baseline differences between session types were not significant for any parameter.

After 6 hours of active patch application, pinprick sensitivity decreased by a mean of 0.42 grades. Compared to both placebo patch and observation only, the reduction in pinprick sensitivity was significant (active vs. placebo patch, p=0.0013; active vs. observation, p=0.0003). Changes in pinprick sensitivity after placebo patch application were not significantly different than observation only. With active patch application, cold sensitivity decreased by a mean of 0.53 grades. Compared to both placebo patch and observation only, the reduction in cold sensitivity was significant (active vs. placebo patch, p=0.0042; active vs. observation, p=0.0001). Cold sensitivity was not significantly changed by placebo patch application. Allodynia was reduced by both active patch application and placebo patch application compared to observation only (p<0.001 for active patch; p=0.02 for placebo patch). Although the decrease was greater with active patch application (mean of individual subject changes; active −0.78, placebo −0.63), the active patch-placebo patch comparison was not significant.

At baseline, the side affected by PHN had abnormal median thermal thresholds compared to the contralateral unaffected area (p<0.0001 for warm threshold, heat pain threshold, cool threshold; p=0.005 for cold pain). When the area affected by PHN was tested 6 hours later during the observation only session, no thermal parameter was significantly different, with all changes being of less than 1° C. in magnitude. Likewise, thermal sensory thresholds on the contralateral unaffected skin did not change significantly when tested 6 hours later.

With active patch application for 6 hours, there were significant changes in cool threshold and cold pain threshold, but not warm threshold or heat pain threshold. The change in warm threshold after active patch application approached significance (overall p=0.059). There was an increase in warm threshold of 1.19° C. after active patch application, compared to decreases (in the direction of improved sensation) of 0.61° C. with placebo patch application and 0.92° C. during the observation only session. With active patch application, the change in heat pain threshold was an increase of 0.42° C., almost identical to the 0.56° C. change with placebo patch application, but neither was significantly different from the 0.02° C. change during the placebo session.

Large changes in perception of cold stimuli were observed after active patch application. There was a 7.9° C. deficit in cool perception (p<0.0001 compared to both placebo patch and observation only) and a 4.9° C. decrease in the threshold for cold pain perception (p=0.002 compared to placebo patch and p<0.0001 compared to observation only). The actual threshold change in cold pain perception was probably larger because for many subjects the median threshold fell to the machine cut-off temperature of 4° C. With placebo patch application and observation only, changes in perception of cooling and cold pain changed less than 1° C.

Symptom Checklist (SCL) and Skin Inspection

Prior to all sessions, symptom checklist (SCL) scores were very low and not significantly different, ranging from a least squares mean of 2.49 to 3.06 out of a maximum of 81. Over the course of the 12 hours of ratings during all session types, the SCL scores changed little. The averaged change in SCL score over the course of the session was −0.93 for active patches, −0.71 for placebo patches, and −0.41 for observation only. There were no significant changes over time within any session type or in pairwise comparisons between session types. The results indicate that new symptoms suggestive of high dose intravenous local anesthetic effects did not occur.

One subject, an elderly man chronically receiving systemic steroids for pulmonary problems, had lasting effects with patch application, consisting of bruising and pain with patch removal. Two subjects had transient (minutes to a few hours) and mild skin reddening, one with placebo and one with active patches. Subjects tolerated peeling the patch(es) off with only minor and very transient increases in pain.

Blood Lidocaine Levels

Levels were reported in nanograms/ml (ng/ml), with the usual minimum anti-arrhythmic level of lidocaine in venous blood being 1000–1500 ng/ml. Blood samples were drawn for lidocaine level in a total of only 98 sessions in which patches were applied, including subjects who did not complete the study, because of venous access problems in a few subjects. In 28 of the 98 sessions (18 active, 10 placebo), lidocaine levels were analyzed with the TDx system. The highest blood level measured with the TDx assay was 70 ng/ml; within the sensitivity, but below the reliable quantitation limit, of the assay. The remaining 70 sessions (46 active, 24 placebo) were analyzed using the more sensitive GC assay. With the GC assay, the highest blood lidocaine level measured after 6 hours application was only 104 ng/ml, indicating minimal systemic absorption of lidocaine. With the GC assay, the highest blood level measured after one hour of patch application was 12 mg/ml. After 4 hours, the highest level was 53 ng/ml. with the lidocaine level exceeding 40 ng/ml in only 7 of the 46 active sessions. After 6 hours application, lidocaine level exceeded 40 ng/ml in 13 of the 46 active sessions.

Intent to Treat Analysis

Although the intent to treat analysis uses only the data from the first session in all subjects beginning any session in order to include data from those subjects not completing the study and to eliminate residual or carryover effects, the results were qualitatively similar to the full analysis. The change in pain intensity VAS scores showed active patch to be superior to observation only at all time points, and superior to placebo patch at 6 hours and 12 hours. Placebo patch was superior to observation only at 2 hours and 4 hours. Category relief scores were higher for active than placebo patches at most time points, but the differences were not significant. Active patches were associated with higher relief scores than observation only at all time points.

Discussion

The mechanism of pain generation in post-herpetic neuralgia is unknown. The present results support the conclusion that spontaneous activity generated in the cutaneous terminals of primary afferents makes an essential contribution to the pain of some patients with PHN. Consistent with this model is the observation that in PHN patients with prominent allodynia, such as those selected for this study, pain and temperature sensation may be relatively unaffected, suggesting intact primary afferents. Furthermore, thermography reveals skin warming in the area of allodynia and maximal pain, possibly resulting from release of vasodilating peptides that are thought to be present in small diameter primary afferents.

It is evident from the above results, that by using lidocaine under conditions where lidocaine is continuously administered intradermally, resulting in maintenance of a therapeutic level of lidocaine for PHN over an extended period of time, substantial relief can be obtained during the period of treatment and, frequently, for substantially longer periods thereafter. In addition, the lidocaine appears to be at a level which does not adversely affect the responsiveness of the neurofibers to other stimuli. Therefore, patients can readily administer to themselves a simple patch, which can be used for a limited period of time under conditions that do not result in interference with their daily activities. In addition, there is no invasive therapy which requires professional administration, nor is there loss of feeling in the region, with accompanying discomforture. Allodynia is also diminished. Few adverse effects are observed, and the treatments can result in long term relief, so as to avoid frequent repetitive application.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for treating neuropathies causing pain at a site with the induction of analgesia by intradermal administration, said method comprising:

applying at the site of pain, a plaster or gel, comprising from about 2 to 10% by weight of lidocaine at least in part as the free base in a formulation which provides for intradermal transport of said lidocaine, whereby said lidocaine is transported intradermally to provide for analgesia at the site of said neuropathy.

2. A method according to claim 1, wherein said formulation comprises at least one of propylene glycol and glycerin as a co-solvent.

3. A method according to claim 2, wherein said co-solvent comprises at least one of D-sorbitol and water.

4. A method according to claim 1, wherein said applying is with a plaster comprising a cover selected from the group consisting of polyvinyl chloride, polyvinylidene chloride, polyethylene, synthetic rubber, woven polyester fabric and non-woven polyester fabric.

5. A method for treating neuropathies causing pain at a site with the induction of analgesia by intradermal administration, said method comprising:

applying at the site of pain, a plaster comprising: a physiologically acceptable adhesive, comprising from about 2 to 10% by weight of lidocaine at least in part as the free base, water, sodium polyacrylate, and propylene glycol, in a formulation which provides intradermal transport of said lidocaine; and a non-woven polyester covering;

whereby said lidocaine is transported intradermally to provide for analgesia at the site of neuropathy.

6. A method according to claim 5, wherein said lidocaine is present in 5% by weight.

7. A method for treating neuropathies causing pain at a site where the induction of analgesia by intradermal administration, said method comprising:

applying at the site of pain, a gel, comprising from about 2 to 10% by weight of lidocaine at least in part as the free base in a formulation which provides for intradermal transport of said lidocaine, whereby said lidocaine is transported intradermally to provide for analgesia at the site of said neuropathy.

*8. A composition for treating neuropathies causing pain at a site by inducing analgesia by intradermal administration, said composition comprising:*

*a plaster or gel comprising from about 2 to 10% by weight of lidocaine at least in part as the free base in a formulation which provides for intradermal transport of said lidocaine.*

*9. The composition according to claim 8, wherein said lidocaine is present in about 5 to 10% weight.*

*10. The composition according to claim 8, wherein said formulation comprises at least one of propylene glycol and glycerin as a co-solvent.*

*11. The composition according to claim 10, wherein said co-solvent further comprises at least one of D-sorbitol and water.*

*12. The composition according to claim 8, wherein said composition comprises plaster which further comprises a cover selected from the group consisting of polyvinyl chloride, polyvinylidene chloride, polyethylene, synthetic rubber, woven polyester fabric and non-woven polyester fabric.*

*13. The composition according to claim 8, wherein said formulation provides for at least 8 hours of analgesia.*

*14. A plaster for treating neuropathies causing pain at a site by inducing analgesia by intradermal administration, said plaster comprising:*

*a physiologically acceptable adhesive, comprising from about 2 to 10% by weight of lidocaine at least in part as the free base water, sodium polyacrylate, and propylene glycol in a formulation which provides intradermal transport of said lidocaine; and a non-woven polyester covering.*

*15. The plaster according to claim 14, wherein said lidocaine is present in about 5 to 10% by weight.*

*16. A gel for treating neuropathies causing pain at a site by inducing analgesia by intradermal administration, said gel comprising:*

*from about 2 to 10% by weight of lidocaine at least in part as the free base in a formulation which provides for intradermal transport of said lidocaine, wherein said formulation comprises 70 to 90% weight of an anhydrous vehicle, 0.1 to 5% weight of a physiologically acceptable gelling agent, 2 to 20% weight of a nonionic surfactant, and up to 10% weight of physiologically acceptable excipients.*

*17. The gel according to claim 16, wherein said lidocaine is present in about 5 to 10% by weight.*

*18. The gel according to claim 16, wherein said anhydrous vehicle is selected from the group consisting of ethanol, isopropanol, propylene glycol, and glycerin.*

*19. The gel according to claim 16, wherein said physiologically acceptable gelling agent is at least one of Carbomer 940 neutralized with diisopropanolamine and neutralized polyacrylic acid.*

*20. The gel according to claim 16, wherein said nonionic surfactant is a sorbitan ester.*

*21. The gel according to claim 16, wherein said formulation further comprises a salicylate compound.*

*22. A patch comprising:*

*a 10×14 cm non-woven polyester backing and a physiologically acceptable adhesive comprising 700 mg of lidocaine base, water glycerin, D-sorbital, sodium polyacrylate, sodium carboxymethyl cellulose, and propylene glycol.*

* * * * *